(12) United States Patent
van Weeghel et al.

(10) Patent No.: US 7,485,433 B2
(45) Date of Patent: Feb. 3, 2009

(54) DETERMINATION AND QUANTIFICATION OF RED BLOOD CELL POPULATIONS IN SAMPLES

(75) Inventors: Robert Paul van Weeghel, Groningen (NL); Roelf Johan Suk, Groningen (NL)

(73) Assignee: IQ Corporation B.V., Groningen (NL)

(*) Notice: Subject to any disclaimer, the term of this patent is extended or adjusted under 35 U.S.C. 154(b) by 220 days.

(21) Appl. No.: 10/791,152

(22) Filed: Mar. 1, 2004

(65) Prior Publication Data

US 2005/0124009 A1 Jun. 9, 2005

Related U.S. Application Data

(63) Continuation of application No. PCT/NL02/00579, filed on Sep. 4, 2002.

(30) Foreign Application Priority Data

Sep. 4, 2001 (EP) .................................. 01203341

(51) Int. Cl.
*G01N 33/00* (2006.01)
(52) U.S. Cl. .................. 435/7.25; 422/61; 422/68.1; 435/7.21; 435/18; 435/287.2; 435/973; 436/15; 436/63; 436/66; 436/172; 436/177
(58) Field of Classification Search .................. 422/61, 422/68.1; 435/7.21, 7.25, 973, 18, 287.2; 436/17, 63, 66, 172, 15, 177
See application file for complete search history.

(56) References Cited

U.S. PATENT DOCUMENTS 5,962,234 A * 10/1999 Golbus ....................... 435/7.1

6,534,279 B1 3/2003 Agthoven et al.

FOREIGN PATENT DOCUMENTS

WO  WO 03/021275 A1  3/2003

OTHER PUBLICATIONS

Taniguchi et al., Carbonic anhydrase isozymes, hemoglobin-F and glutathione levels in lead-exposed workers, Clinica Chimica Acta: International Journal of Clinical Chemistry, (Feb. 22, 1975) vol. 59, No. 1, pp. 29-34.*
Funakoshi et al., Human Carbonic Anhydrases, the Journal of Biological Chemistry 245 (11): 2852-2856 (1970).*
Tamachi, Immunological Determination of Human Fetal Hemoglobin, Z. Klin. Chem. Klin. Biochem. 11: 501-505 (1973).*

(Continued)

*Primary Examiner*—Gailene R Gabel
(74) *Attorney, Agent, or Firm*—TraskBritt

(57) ABSTRACT

The invention relates to the detection and determination of erythrocytopathies and hemoglobinopathies. The invention provides a method for distinguishing between subsets of red blood cells in a sample involving contacting the sample with at least a first marker reagent reactive with a first component of a red blood cell and with at least a second marker reagent reactive with a second component of a red blood cell and determining the reactivity of the marker reagents with the cells.

4 Claims, 5 Drawing Sheets

OTHER PUBLICATIONS

PCT International Search Report, PCT/NL02/00579, dated Nov. 7, 2002.

PCT International Preliminary Examination Report, PCT/NL02/00579, dated Jul. 16, 2003, 3 pages.

Davis, et al., Detection of fetal red cells in fetomaternal hemorrhage using a fetal hemoglobin monoclonal antibody by flow cytometry, Immunohematology, Aug. 1998, pp. 749-756, vol. 38.

Brady et al., Expression of the human carbonic anhydrase I gene is activated late in fetal erythroid development and regulated by stage-specific trans-acting factors, British Journal of Haematology, 1990, pp. 135-142, vol. 76.

Kondo et al., Estimations of Active and Inactive Carbonic Anhydrase Isozyme B in Human Red Cells, Clinica Chimica Acta, May 1975, pp. 347-353, vol. 60, No. 3.

Taniguchi et al., Carbonic Anhydrase Isozymes, Hemoglobin-F and Glutathione Levels in Lead-exposed Workers, Clinica Chimica Acta, 1975, pp. 29-34, vol. 59, No. 1.

Tamachi, Immunological Determination of Human Fetal Hemoglobin, Z. Klin. Chem. Klin. Biochem., 1973, pp. 501-555, vol. 11, No. 12.

\* cited by examiner

DETERMINATION AND QUANTIFICATION OF RED BLOOD CELL POPULATIONS IN SAMPLES

CROSS-REFERENCE TO RELATED APPLICATION

This application is a continuation of PCT International Patent Application No. PCT/NL/02/00579, filed on Sep. 4, 2002, designating the United States of America, and published, in English, as PCT International Publication No. WO 03/021275 A1 on Mar. 13, 2003, the contents of the entirety of which is incorporated by this reference.

TECHNICAL FIELD

The invention relates generally to biotechnology, and more particularly to the detection and determination of erythrocytopathies and hemoglobinopathies.

BACKGROUND

The detection of circulating fetal cells in maternal blood samples represents an important area of laboratory support to the obstetrical management of women. Although the concentration of fetal erythrocytes found in the maternal blood circulation during pregnancy is mostly very small and without a clear clinical significance in many cases, substantial hemorrhage may result from a number of causes including fetal or maternal trauma and placental defects (1). The quantification of fetal red blood cells (RBCs) is most commonly used to estimate the degree of feto-maternal hemorrhage (FMH), either in cases of trauma with suspected placental injury or in the situation of RhD incompatibility between the fetus and the mother for prevention of hemolytic disease of the newborn (HDN) during pregnancy (2, 3). The obstetrical management of women includes the prevention of mother immunization against a foreign fetal cell antigen and the monitoring of maternal antibody concentration. To prevent an immune response, an immunoprophylaxis based on anti-RhD polyclonal antibodies is given to the mother at a dose proportional to the estimated count of fetal RBCs present in the maternal blood circulation (4, 5). It is, therefore, important to be able to at least semi-quantify the relative amount of the cells.

Most clinical laboratories perform FMH estimates on the basis of variations of the slide-based microscopic counting method of acid elution originally described as the Kleihauer-Betke test (6). Although this assay has proven to be clinically useful in the detection of large episodes of FMH requiring maternal treatment with more than the standard dose of Rh-immune globulin, it is laborious and suffers from subjectivity and imprecision (7, 8). Besides the experience of the laboratory technicians for interpretation of the results, the test has a tendency to overestimate the size of feto-maternal hemorrhages because maternal HbF-containing RBCs or F-cells are counted within the population of fetal cells (9).

Several alternative and more accurate screening methods to detect FMH using flow cytometry have been proposed and described. The first reports investigating the feasibility of using flow cytometry for fetal cell counting primarily relied upon the detection of the human D antigen on the cell surface of RBCs (10, 11, 12, 13). These approaches all demonstrated greater sensitivity and precision than manual methods. However, the use of anti-RhD is applicable only to the clinical situations with Rh or D antigen incompatibility and cannot be utilized in all cases of maternal trauma and suspected FMH. Several other methods for flow cytometric detection of fetal cells in maternal peripheral blood have recently been described. The methods differ in their means of using various cellular fixation and permeabilization steps, usually in combination with the intracellular detection of fetal hemoglobin (HbF) antigen using anti-HbF antibodies.

As an increase of the expression of fetal hemoglobin (HbF) in peripheral red blood cells is also a common feature in hemoglobinopathies comprising genetic disorders of hemoglobin such as sickle-cell disease and beta-thalassemia (14, 15, 16, 17), a method for the detection of HbF in blood cells also finds its use in the diagnosis of hemoglobinopathies other than those related to FHM.

DISCLOSURE OF INVENTION

The invention includes a method of distinguishing between subsets of red blood cells in a sample, the method comprising contacting the sample with at least a first marker reagent reactive with a first, preferably antigenic, component of a red blood cell and with at least a second marker reagent reactive with a second, preferably antigenic, component of a red blood cell and determining the reactivity of the markers with the cells.

In a preferred embodiment, the invention provides a method for distinguishing between and/or quantification of various subsets of erythrocytes in a sample comprising the use of at least two markers reactive with at least two subsets of red blood cells, such as HbF-containing erythrocytes (F-cells) or fetal versus adult red blood cells in blood. To diagnose or assess FMH, the invention thus provides for distinguishing between subsets of red blood cells in a sample comprising combining testing for a determinant of essentially fetal cells with a determinant for essentially adult cells. Various subsets may overlap in that some cells in each subset carry two of the markers used in the method chosen. The method is most useful to distinguish between subsets of mature erythrocytes, i.e., those that have matured beyond the nucleated RBC or immature reticulocyte phase.

In one embodiment, the invention provides a method for distinguishing between and/or quantification of fetal red blood cells (RBCs) in maternal blood comprising the use of at least two markers reactive with various subsets of red blood cells.

In another embodiment, the invention provides a method for distinguishing between and/or quantification of adult HbF-containing RBCs in blood comprising the use of at least two markers reactive with various subsets of red blood cells. In spite of the recent reported results of the detection of fetal HbF-containing cells in different maternal blood samples, the use of a single parameter does not offer an accurate and reliable quantification of fetal RBCs and maternal F cells. A dual or multiple marker approach has several advantages. Although the use of HbF antigen as single marker allows broad application for fetal red blood cell detection to many clinical situations, the use of anti-HbF by itself provides the possibility of an overestimation of the proportion of true fetal cells in a given HbF population. Use of the intracellular cell marker Carbonic anhydrase (CA) for adult RBCs (18) in combination with HbF should allow, for example, the clear distinction of fetal red blood cells from possible interfering maternal F cells that have a lower cellular HbF content and are positive for the CA marker. Small populations of adult erythrocytes containing HbF are found in individuals of any age; these cells have been termed F cells. For people with sickle cell anemia, these cells are functionally quite important because they are capable of transporting and releasing oxygen.

A method is provided for distinguishing between subsets of red blood cells in a sample comprising contacting the sample with at least a first marker reagent reactive with a first component of a red blood cell and with at least a second marker reagent reactive with a second component of a red blood cell and determining the reactivity of the marker reagents with the cells. Suitable cell surface components to be detected are, for example: CD71, a type II membrane glycoprotein of 90-95 kDa that exists as a homodimer on most dividing cells including RBCs (the protein plays a critical role in the uptake of iron through the binding and endocytosis of transferrin, the major iron-carrying protein); GpA, a cell surface sialoglycoprotein of 41 kDa that is exclusively expressed on human erythroid cells and their progenitors (the GpA protein is clinically important in the classification of acute leukemias); and a glycosylated Lewis antigen structure expressed on adult T- and B-lymphocytes and fetal lymphocytes and RBCs during the first eight months of development.

For some applications, such as flow cytometric detection, it is preferred that at least one of the components to be detected comprises an intracellular component. Suitable intracellular components are, for example, HbE, an intracellular hemoglobin protein consisting of four protein subunits of approximately 140 amino acids. The embryonic hemoglobin tetramer further consists of different polypeptide chains, epsilon and zeta or epsilon and alpha. The expression of HbE is most prominent in embryonic red blood cells. CA, Carbonic anhydrases (carbonate dehydratase, carbonate hydrolyase) form a large family of genes encoding zinc metalloenzymes of great physiologic importance. As catalysts of the reversible hydration of carbon dioxide, these enzymes participate in a variety of biologic processes, including respiration, calcification, acid-base balance, bone resorption, and the formation of aqueous humor, cerebrospinal fluid, saliva, and gastric acid. CAs are encoded by members of three independent CA gene families, i.e., alpha-CA, beta-CA, and gamma-CA. Genes in the alpha-carbonic anhydrase family encode either active carbonic anhydrase isozymes or "acatalytic" (i.e., devoid of $CO_2$ hydration activity) carbonic anhydrase-related proteins. Alpha-carbonic anhydrases show extensive diversity in tissue distribution and in their putative or established biologic functions. Some of the alpha-CAs are expressed in almost all tissues (e.g., CA 2), whereas some show a more restricted expression, such as CA 1 in erythrocytes. Erythrocyte carbonic anhydrase has two isoenzymes with different amino acid sequences and specific activities. B and C were the original designations for these two major forms which later were called CA I (or A) and CA II (or B), respectively. In cells, carbonic anhydrases may reside in cytoplasm, in mitochondria, or in secretory granules, or associate with membranes.

Such an intracellular component to be detected can be the whole component per se, or can, for example, be the intracytosolic part of a protein or receptor that otherwise projects or extends through the cell membrane. For intracellular detection of intracellular components, fixation and permeabilization of the red blood cells is required. This advantageously provides rigidity and stability to the erythrocytes to be identified. Detecting intracellular antigens in fixed erythrocytes thus allows for less background noise than detecting extracellular antigens in non-fixed cells only. A preferred method is using a combination of two intracellular components (target proteins or antigens) to discriminate between different red blood cell populations of, for example, fetal, parental or adult origin.

In a preferred embodiment, the invention provides a method wherein the first component consists of hemoglobin F. Hemoglobin (Hb) is an intracellular protein consisting of four protein subunits of approximately 140 amino acids. The fetal hemoglobin tetramer further consists of different polypeptide chains, gamma and zeta or gamma and alpha. The expression of HbF is essentially fetal, in that it is most prominent in fetal red blood cells, but is also present in low concentrations in adult red blood cells. HbF is red blood cell specific. Because of the precise discrimination between the cell populations with HbF and another intracellular protein, the invention provides a method for nearly truly quantifying the true fetal cells and not to include or to count possible interfering adult F cells. In another preferred embodiment, the invention provides a method wherein the second component consists of carbonic anhydrase B. Carbonic anhydrase is a protein or metalloenzyme with a catalytic activity for $CO_2$. The expression of CA is essentially or predominantly in adult cells. Much preferred (and further explained in the detailed description herein) is a method wherein the first component consists of hemoglobin F and the second component consists of carbonic anhydrase, especially wherein the carbonic anhydrase is of type 1.

A marker reagent used in a method according to the invention can comprise any kind of binding molecule, such as phage-derived binding molecules (sometimes also called "phage antibodies"), but preferred is a method wherein at least one of the marker reagents comprises an antibody. An antibody, in the format of complete Ab or Fab, Fv, sFv, camel-derived single chain or other protein structure, is a protein that comprises a so-called light chain and/or a heavy chain or chains which are each, or in combination, responsible for the specific binding of the target antigen. A particularly useful anti-HbF antibody is specific for the gamma protein subunit of hemoglobin F. Antibodies raised against the i antigen are most often specific for this surface protein in the glycosylated form. Monoclonal antibody CD71 is directed towards the transferrin receptor, while anti-GpA antibodies recognize an epitope on the Glycophorin A antigen. Another useful antibody is specific for the epsilon polypeptide chain of embryonic hemoglobin (HbE). Antibodies raised against CA isotypes are specific for the several epitopes present on the different carbonic anhydrases. It is, of course, preferred for ease of detection that at least two or all of the marker reagents comprise an antibody, each of the antibodies being reactive with a distinct antigenic component of a red blood cell. After fixation and permeabilization, the antibody will enter the cell and bind to the intracellular fixed target protein.

Another type of marker reagent according to the invention comprises a non-proteinaceous molecule which can bind with high specificity to a target component, like an inhibitor that can bind to a target enzyme. For example, a sulfonamide inhibitor can be complexed to carbonic anhydrase via the coordination of a primary sulfonamide group to the active site zinc ion (19). Detection of such a marker reagent bound to a target is most easily achieved by using a labeled inhibitor, for example, a fluorescent derivative of the inhibitor. A useful marker reagent for detecting a target protein according to the invention is a fluorescent inhibitory molecule which labels cells at a low concentration, like in the nanomolar range, and with a short loading time, e.g., within ten minutes. Also, the efficacy of such an inhibitor should remain essentially unchanged by the fluorescent label. A particularly suitable marker reagent to practice the present invention comprises Bodipy 558/568-modified acetazolamide, a fluorescent inhibitor of CA (20). This modified acetazolamide was used to localize CA in living osteoclasts and can be obtained from Molecular Probes (Eugene, Oreg.) or similar companies. In one embodiment, the invention provides a method to distinguish fetal cells from maternal blood using an antibody against HbF as a first marker reagent and a fluorescent CA inhibitor as a second marker reagent.

In another embodiment, fetal cells are identified through the use of a marker reagent capable of binding to an intracellular component wherein the component is a nucleic acid. The term "nucleic acid" as used herein, refers to either DNA or RNA. For example, nucleic acid probes are useful to detect the presence of a specific nucleic acid sequence in a cell. A variety of methods for specific DNA and RNA measurement using nucleic acid hybridization techniques are well known. For example, a method for evaluating the presence of a certain nucleic acid in a sample involves the use of fluorescent in situ hybridization (FISH) technology. Hereto, a sample is contacted with a fluorescent-labeled probe having a nucleic acid sequence complementary to the RNA or DNA sequence of interest. Subsequently, hybridization of a probe to a nucleic acid can be measured by a fluorescence detection system, e.g., by fluorescent microscopy or flow cytometry. A rapid and sensitive FISH method has been developed to probe RNA or DNA contents of individual cells by flow cytometry. Fixed cells in suspension were hybridized with 5' end-fluorochrome-labeled oligodeoxynucleotides complementary to defined regions of the nucleic acid of interest and analyzed by flow cytometry (21). The present invention can, for instance, be practiced using a HbF antibody as a first reagent marker and a 5' end-fluorescein-conjugated oligodeoxynucleotide probe complementary to a stretch of carbonic anhydrase mRNA as a second marker agent. Oligonucleotides labeled with another fluorochrome, such as coumarin, rhodamine, phycoerythrin, Texas Red and the like, may also be used.

As stated, marker reagents, being antibodies or other binding molecules, are most easily detected when labeled. Detection via a label that comprises a fluorochrome is useful.

A fluorochrome to be used may be any of the known molecules used in flow cytometry and or microscopy. Examples of fluorochromes are protein labels like R-PE, APC, GFP, and chemical labels like Alexa dyes, Cy dyes, tandem labels between the mentioned dyes, or others. Most of the dyes may be purchased from Molecular Probes or similar companies. Preferred is a method wherein at least two of the marker reagents comprise a fluorochrome, each of the fluorochromes having a distinct emission spectrum. Emission spectra preferably range from 350 to 800 nm. Enzymes (peroxidase, alkaline phosphatase and others) are generally naive or recombinant proteins which can also be attached to antibodies or other marker reagents (labeled) and used to visualize color development with different fluorescent or non-fluorescent substrates like the 2-(5'-chloro-2'-phosphoryloxyphenyl)-6-chloro-4-(3H)-quinazolinone (termed ELF-97 phosphate), tetramethyl benzidine (TMB) and others, which may be purchased from Molecular Probes, Pierce and others.

Preferred is a method as provided herein further comprising determining the reactivity of the marker reagents with the cells by flow cytometry, i.e., by detecting the reactivity of the marker reagents with the cells by detecting fluorescence.

The invention also provides a diagnostic kit suitable for the differentiation of subsets of erythrocytes, the kit at least comprising a first marker reagent reactive with a first component of a red blood cell and a second marker reagent reactive with a second component of a red blood cell, preferably wherein the first component consists of hemoglobin F and/or wherein the second component consists of carbonic anhydrase.

Type I carbonic anhydrase is preferred for reasons explained above. The marker reagent is preferably an antibody, but can in essence be any binding molecule with the desired binding specificity, the antibody or binding molecule being reactive with a distinct, preferably intracellular and antigenic component of a red blood cell. The kit can also comprise the desired fluorochrome or several distinct fluorochromes having a distinct emission spectrum.

The invention also provides a reagent mixture suitable for inclusion in such a kit and suitable for the differentiation of subsets of erythrocytes, the reagent mixture at least comprising a first marker reagent reactive with a first component of a red blood cell and a second marker reagent reactive with a second component of a red blood cell, preferably wherein the first component consists of hemoglobin F and/or wherein the second component consists of carbonic anhydrase. Type I carbonic anhydrase is preferred for the reasons explained above.

In the detailed description, a highly accurate and quantitative procedure for the detection of distinct populations of fetal and F cells by flow cytometry that can be routinely performed is reported. The description further illustrates that the use of a dual-fluorescent parameter assay, based on the combined detection of fetal hemoglobin (HbF) and carbonic anhydrase (CA), is able to separate true fetal RBCs from interfering maternal F cells.

Furthermore, a fetal antigen, or fetoprotein, also occurs in adults in certain diseases. For example, an increase of the expression of fetal hemoglobin (HbF) in peripheral red blood cells is a common feature in hemoglobinopathies comprising genetic disorders of hemoglobin such as sickle cell disease and beta-thalassemia. The invention also provides a method for the detection of HbF or another fetoprotein in red blood cells in samples of a subject with a disease such as hemoglobinopathy.

A method according to the invention also finds its use in the field of non-invasive prenatal testing. Prenatal testing includes quantitative or qualitative diagnostics or prenatal evaluation, including determining the sex of the fetus, determining chromosomal, single gene or protein abnormalities, and determining the presence or absence of particular genes, nucleic acids or proteins. To date, there are more than 300 different disorders that can be detected during pregnancy. Some of these are chromosomal abnormalities such as Down syndrome; some are single gene disorders such as cystic fibrosis, Tay-Sachs disease and sickle cell disease. Currently, prenatal diagnosis of chromosome abnormalities requires invasive techniques such as amniocentesis and chorionic villus sampling that carry small but finite risks of fetal loss. A non-invasive approach is to isolate fetal cells from maternal blood by flow sorting followed by genetic interphase analysis with fluorescence in situ hybridization (FISH). A non-invasive method of prenatal genetic diagnosis requires fetal cell selection from the maternal circulation that allows efficient recovery of fetal cells for FISH analysis. The candidate cell is in general a fetal nucleated red blood cell (NRBC). A current method for enrichment of NRBCs involves initial separation of blood on a density gradient, white cell depletion using a panning technique with a CD45 monoclonal antibody followed by flow sorting based either on selection for CD71+, CD45−, and LDS-751 or gamma-hemoglobin (22). As mentioned before, discrimination between fetal and maternal blood cells on the basis of a single marker is often problematic. Prenatal diagnostics of this type obviously require an optimal separation of fetal cells from maternal cells. Current prenatal diagnostics are often hampered by a poor identification of maternal and fetal subpopulation of cells in a maternal blood sample. In one embodiment of the invention, a method is provided for non-invasive prenatal testing of a fetus, the method comprising the steps of identifying and isolating fetal cells from a maternal blood sample according to the invention and testing the fetal cells.

The present invention provides a highly accurate and sensitive method to identify and/or isolate fetal cells that circulate in the maternal blood that is based on a combination of two marker reagents. A dual-color flow cytometric method allows simultaneous detection of these two reagents. Use of a method as provided allows identifying and isolating a population of fetal cells from maternal cells with a high sensitivity and accuracy. In a preferred embodiment, cells in a maternal blood sample are stained with an anti-HbF antibody as a first marker reagent and an antibody reactive with CA as a second marker reagent. Fetal RBCs are recognized by their bright HbF staining in combination with a complete absence of CA expression. Subsequently, this HbF-positive, CA-negative population, corresponding to fetal blood cells, can be separated from maternal cells by flow sorting. Flow sorting may be performed using normal or high-speed multi-parameter flow cytometry/cell sorting. Thereafter, isolated fetal cells can be expanded first by in vitro culturing or they may be analyzed directly for, e.g., chromosomal abnormalities.

In another embodiment, an embryonic cell marker is used together with an anti-CA antibody to identify an embryonic RBC population that circulates in a pregnant woman's blood stream. For example, such a procedure can be used to isolate embryonic cells, like erythroblasts, by flow cytometric cell sorting. Embryonic cells may subsequently be subjected to prenatal diagnostics, for example, they can be treated to render the embryonic nucleic acids and/or proteins available for identification and/or amplification. Such a method allows a quantitative or qualitative diagnostic or prenatal evaluation at a very early stage of embryonic development, e.g., as early as six weeks after conception. Use of anti-embryonic epsilon Hb antibodies as a marker reagent to identify fetal cells is sometimes preferred. In a preferred embodiment of the present invention, a first marker reagent reactive with embryonic hemoglobin (HbE), for example, an antibody directed against the epsilon chain of HbE, is preferably combined with a second marker reagent reactive with CA to detect and/or isolate the rare population of embryonic cells which circulate in a pregnant woman's blood stream. Other suitable embryonic or fetal markers which may be used in the invention are characterized in their temporal expression pattern. Preferably, such a marker comprises an intracellular protein which is highly expressed in embryonal and/or fetal cells whereas its expression is strongly reduced or essentially non-existing after birth. These may include apoptosis-related proteins, such as survivin, transcription factors, like a transcription factor of the basic helix-loop-helix (bHLH) family or a GATA (-like) transcription factor.

Furthermore, a method provided in the invention finds its application in other clinical situations, such as intrauterine transfusion (IUT). IUT allows blood transfusions and/or medications to be administered to the baby while in the uterus. Blood transfusion by IUT has, for example, been used over the last three decades to treat fetal anemia caused by Rhesus incompatibility. IUT has become increasingly common and relatively safe since the development of high-resolution ultrasound. The efficacy of IUT can be assessed by taking fetal blood samples and staining fetal cells. The fetal circulation is usually accessed through the placental cord insertion although a free loop or fetal cord insertion can also be used. By fetal cell staining, the percentage of the donor's red cells in the fetal circulation can be determined. The use of a single marker reagent such as an anti-HbF antibody bears the risk of overestimating the proportion of true fetal cells in a given HbF population. As exemplified herein, a method using two marker reagents as provided herein allow for distinguishing of fetal cells from small, yet significant, populations of adult cells containing HbF, also termed F cells. Thus, the invention provides a method to produce accurate data of true fetal cell frequency for monitoring the efficacy of a clinical procedure like IUT. For example, the method provided permits quantifying fetal cells in a fetal blood sample and calculating the percentage of a donor's red cells in the fetal circulation. In yet another embodiment of the invention, a method according to the invention finds its use in monitoring abnormal fetal cell trafficking in preeclampsia and other pregnancy-related disorders.

As exemplified in the detailed description, the dual-flow cytometric procedure provided herein shows an excellent linearity and precision both below and above the clinically important fetal cell frequency of 0.6%. Serial dilutions of mixtures of cord blood and adult blood with a fetal cell frequency range of 0 to 5% were analyzed. Precision was evaluated by performing ten replicates on each sample within a five-day period; this consistently demonstrated a coefficient of variation (CV) of <5%. In a preferred embodiment, the method provided herein has a CV of <10% for blood samples with >0.1% fetal cells, more preferred a CV of <7%, most preferred a CV of <5%.

Flow cytometric analysis allows for the analysis of several different clinical samples, like up to five or even up to seven different test samples, in an hour or less and thus provides a relatively straightforward method amenable to clinical use. The dual-flow cytometric method according to the invention provides a technically superior alternative to existing one-color-flow cytometric procedures. The method provided allows analysis of a large number of cells in a relatively short time compared to other detection techniques such as visual inspection of each test sample by fluorescent microscopy. Also, with respect to ease of use in common clinical laboratories, flow cytometry is now preferred over microscopy.

Taken together, the method for distinguishing between red blood cells provided in the invention has an improved performance and is easier and faster in its use compared to existing procedures.

BRIEF DESCRIPTION OF THE DRAWINGS

FIG. 3D demonstrates the separation of the interfering adult F cells (R8) from the true fetal cells in R10.

DETAILED DESCRIPTION OF THE INVENTION

Figure 1:
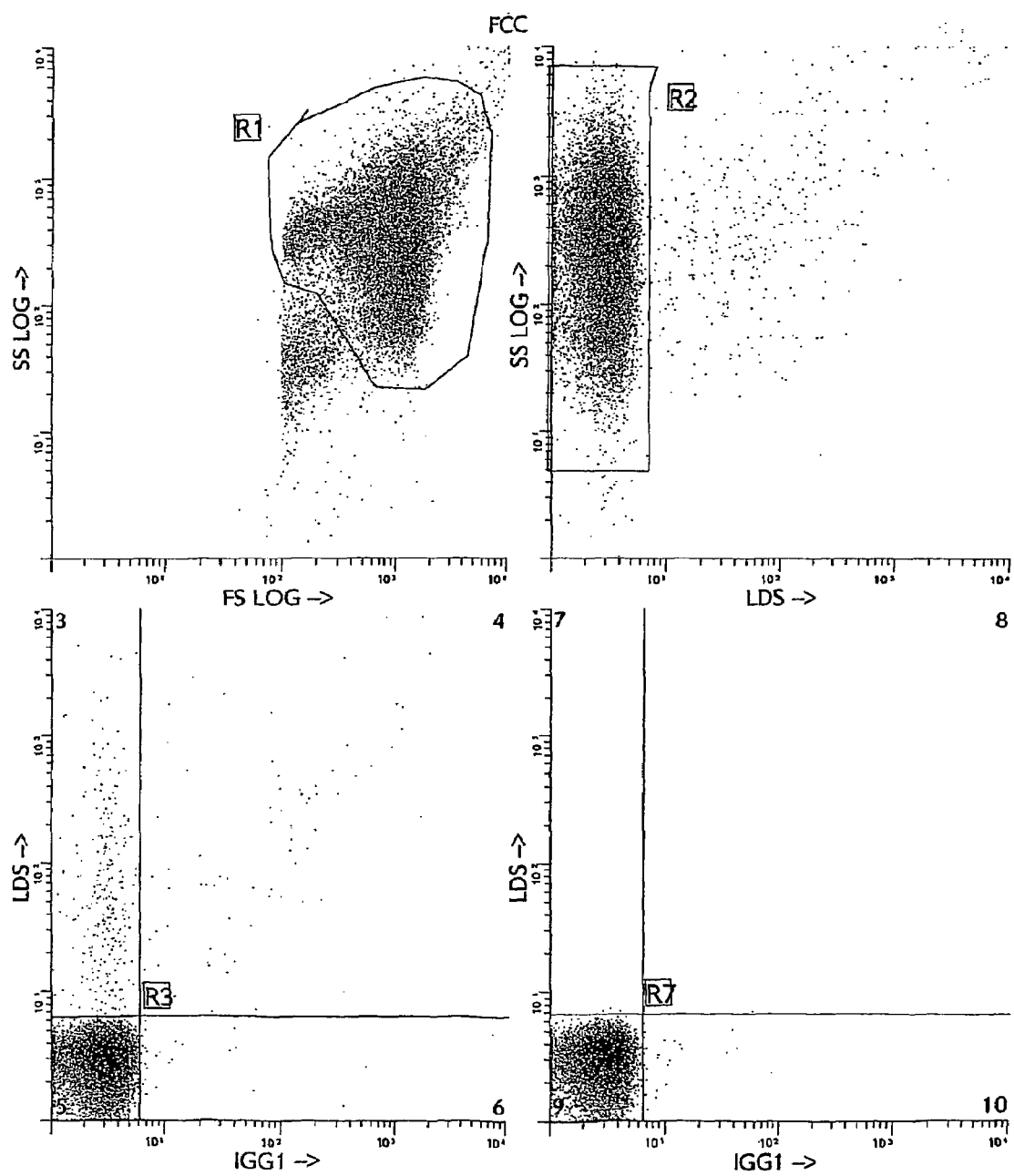
FIG. 1 shows cytograms demonstrating the population of contaminating autofluorescent WBCs that can be detected and separated by the DNA-staining dye LDS-751.

Several alternative and more accurate screening methods to detect FMH using flow cytometry have been proposed and described. The first reports investigating the feasibility of using flow cytometry for fetal cell counting primarily relied upon the detection of the human D antigen on the cell surface of RBCs (10, 11, 12, 13). These approaches all demonstrated greater sensitivity and precision than manual methods. However, the use of anti-RhD is applicable only to the clinical situations with Rh- or D-antigen incompatibility and cannot be utilized in all cases of maternal trauma and suspected FMH. Several other methods for flow cytometric detection of fetal cells in maternal peripheral blood have recently been described (14, 15, 16, 17). The methods differ in their means of using various cellular fixation and permeabilization steps, in combination with the intracellular detection of HbF antigen using anti-HbF antibodies. The flow cytometric anti-HbF approach has several potential advantages and the HbF antigen allows broad application of flow cytometric fetal red blood cell detection to many clinical situations. Furthermore, the anti-HbF method provides good correlation with the standard Kleihauer-Betke test of fetal cell detection, although with a much higher precision than the manual acid elution assay. However, our findings with the approach of one cell marker such as HbF indicated that this single-color assay was not precise enough for the enumeration of true fetal cells and could not rule out the inclusion of a low percentage of false-positive F cells. A small population of 2 to 8% adult cells containing low amounts of HbF was observed. Separation and a clear distinction of both populations of fetal HbF-containing cells and interfering adult F cells with a lower HbF content is very important in order to produce accurate data of true fetal cell frequency in maternal blood for FMH assessment or F cell measurements.

Our findings describe an alternative approach to flow cytometric quantification of fetal RBCs using antibodies to the intracellular located Fetal Hemoglobin (HbF) and Carbonic anhydrase (CA), and an optimal intracellular staining technique. The method or procedure is based on the discrimination between fetal and adult red blood cells using specific anti-Carbonic anhydrase (CA) polyclonal and monoclonal anti-HbF antibodies. The HbF antigen/protein is the best marker for the detection of fetal red blood cells, while the CA antigen/protein is a good marker for adult red blood cells and is almost absent in fetal red blood cells. The monoclonal and polyclonal antibodies used in the test are fluorochrome-conjugated for direct and indirect detection of HbF and CA markers in a dual-flow cytometry analysis. Both antibody preparations were shown to be specific for HbF and CA, respectively, using the protocol as described in the material section. No positive cell staining was ever demonstrated without permeabilization of the cells.

The preliminary results from the dual-color flow cytometric method were comparable to those in some previous reports describing anti-HbF data. The F cell percentages in whole blood of normal donors obtained during the study were also comparable to those in previous reports. Our findings demonstrate that by adding a second unique cell marker such as Carbonic anhydrase to the HbF flow cytometric method, it is possible to identify distinct populations of red blood cells. The new method is able to discriminate between true fetal cells and possible false-positive F cells, by shifting the small population of HbF-containing F cells from the fetal cell population to the larger population of CA-positive adult cells. The complete dual-color staining and analysis of up to five samples can be easily performed within 1.5 hours of blood collection. The accurate detection of HbF-containing fetal red blood cells in maternal blood circulation will aid to estimate the degree of feto-maternal hemorrhage (FMH) in women during pregnancy, and subsequently in the management of hemolytic disease of the newborn (HDN).

Finally, the new and sensitive flow cytometric method using a dual-fluorescent-staining procedure, will accurately identify and quantify both interfering maternal F cells and fetal red blood cell populations. In agreement with other studies (14, 15, 16, 17), it represents a practical and technically superior alternative for the routine measurement of feto-maternal hemorrhage compared to the more subjective and manual Kleihauer-Betke test.

Materials and Methods

Specimen Collection

Whole blood of 0.5 to 1 ml from normal donors as well as cord blood was collected on EDTA. The samples were usually assayed on the same day or stored at 4-8° C. for one week before testing.

Antibodies and Reagents

Monoclonal antibody NaM16-2F4 (mouse IgGl) specific for the gamma chain of human HbF was previously described (14) and purchased from Bioatlantic (Nantes, France). Pure antibody preparations were directly conjugated to R-phycoerythrin (R-PE) following standard labeling procedures. Its PE-conjugated IgGl isotype control was purified and labeled using standard labeling procedures. Polyclonal goat anti-human carbonic anhydrase was purchased from AbCAM while the FITC-conjugated anti-goat was obtained from Sigma. LDS-751 DNA-staining dye was purchased from Molecular Probes and stored at 4° C. until use. Newborn calf serum was purchased from Greiner. All other reagents were of analytical grade.

Cell Fixation and Permeabilization

Ten microliters of whole blood or cord blood were resuspended into 100 μl of newborn calf serum (NCS) in PBS, after which the RBCs were fixed with 100 μl of 20% paraformaldehyde in PBS, vortexed for five seconds, and incubated at room temperature (RT) for 30 minutes. After fixation, the cells were washed once with 2 ml of PBS with heparin and resuspended in 100 μl of PBS with heparin. For permeabilization of the RBCs, 100 μl of fixed cells were mixed thoroughly with 100 μl of 0.3% sodium dodecyl sulfate (SDS) in PBS with heparin and allowed to stand at RT for 3 minutes. To remove the SDS, the cells were washed twice with 2 ml of PBS with heparin and suspended in 1 ml of the same solution.

HbF and CA Detection by Flow Cytometry

For immunophenotyping, 100 μl of the washed cell suspension was then mixed with either 50 μl anti-HbF-PE MoAb diluted at 40 μg/ml in PBS, 50 μl of anti-Carbonic Anhydrase PoAb diluted 1-in-500, and 50 µl of LDS-751, or 100 µl of the washed cell suspension was mixed with 50 µl of LDS-751 and 50 µl of PBS and 50 µl isotype control as a negative control. After an incubation of 15 minutes at RT in the dark, cells were washed once with 2 ml PBS-containing heparin. Then 100 µl suspended cell solutions were both mixed with 50 µl of anti-Goat IgG-FITC and incubated at RT for 15 minutes. The cells were washed to remove the secondary labeled conjugate and finally resuspended in 0.5 ml of PBS with heparin, ready for flow cytometry. The isotype control was used instead of the anti-HbF MoAb for a negative control.

Sample acquisition was performed on a Coulter Epics XL MCL flow cytometer (Beckman-Coulter, U.S.A.). The HbF and CA cells were counted by setting the autostop at 50,000 or 100,000 events, with the collection of measures of logFSC and logSSC, and fluorescence signals of logFL1, logFL2 and logFL4 as list mode files.

Data analysis was performed with software (Winlist, Verity Software, Topsham, ME) on list mode files. The live gate on LDS-751-negative cells was used to exclude possible interfering nuclei-containing white blood cells. The positive cut-off point was approximately at 0.5% above negative population of isotype control staining cells.

Results

A dual-color flow cytometric method results in the simultaneous detection of two intracellular antigens and provides a convenient and rapid test that can be completed within 1.5 hours of blood collection. The use of paraformaldehyde as a fixative reagent and sodium dodecyl sulfate (SDS) to permeabilize fixed RBCs resulted in low background staining, negligible HbF leakage, and minimal cell clumping. Following fixation and permeabilization, both cell antigen markers could be detected with high fluorescence signals, which resulted in a clear distinction between different stained cell populations.

An important aspect of the flow cytometric fetal cell count data is to exclude possible interfering adult hemoglobin containing RBCs and auto-fluorescent WBCs present from the region of fetal cell identification. The induced auto-fluorescent WBCs can be readily excluded from the fetal cell population by staining these nuclei-containing cells with a DNA-staining dye such as LDS-751 as shown in FIG. 1.

Figure 2:
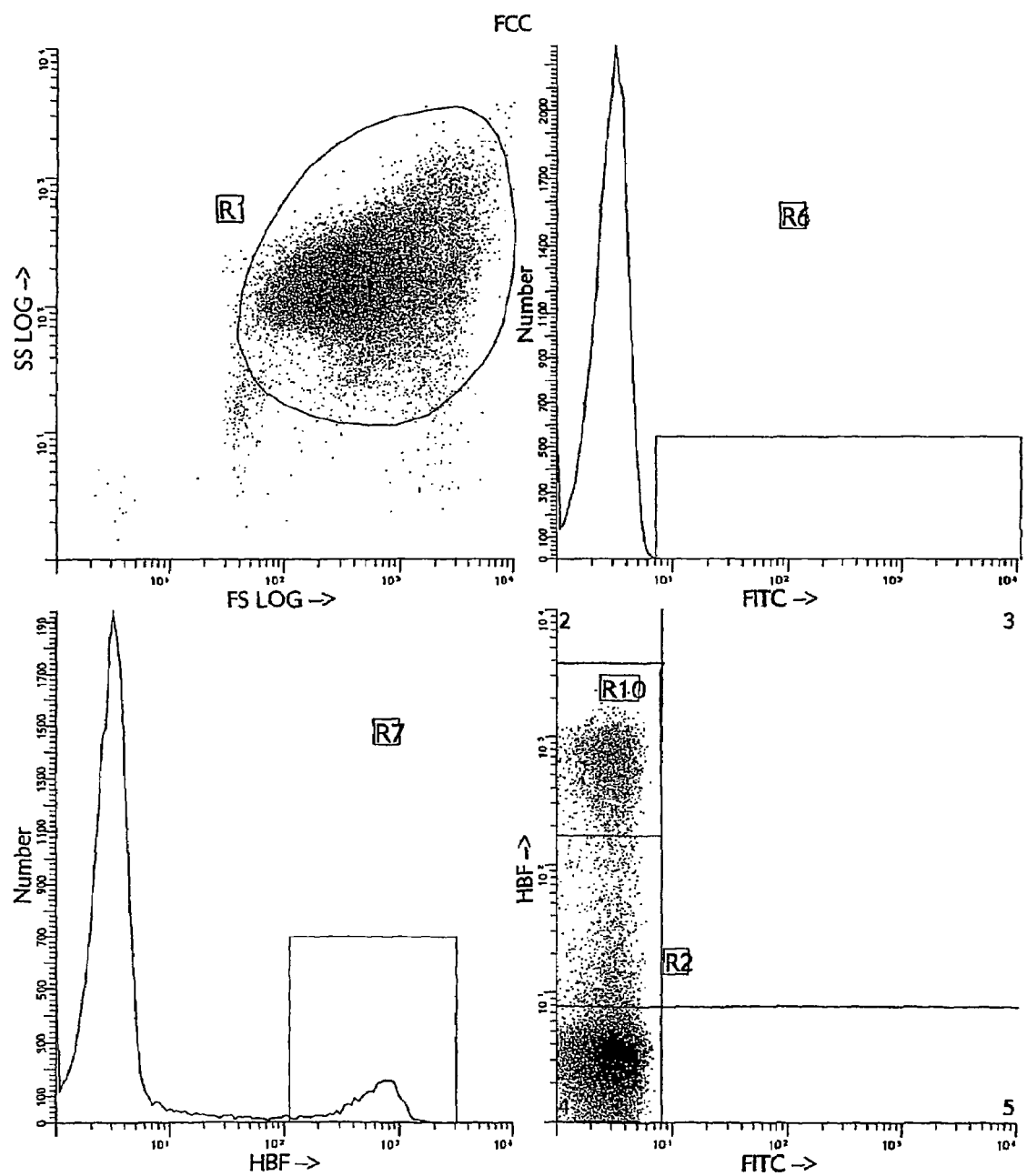
FIG. 2 includes cytograms representative of 10% cord blood mixed with normal adult blood and stained with monoclonal antibody directed to HbF. The distributions of fetal HbF+++ cells, adult HbF+ cells and adult HbF− cells are indicated in the different cytograms. The interfering population of adult F cells (HbF+) are difficult to separate from the fetal RBCs in R10 and negative-stained adult cells (HbF−) in four, as demonstrated in FIG. 2D.
Figure 3:
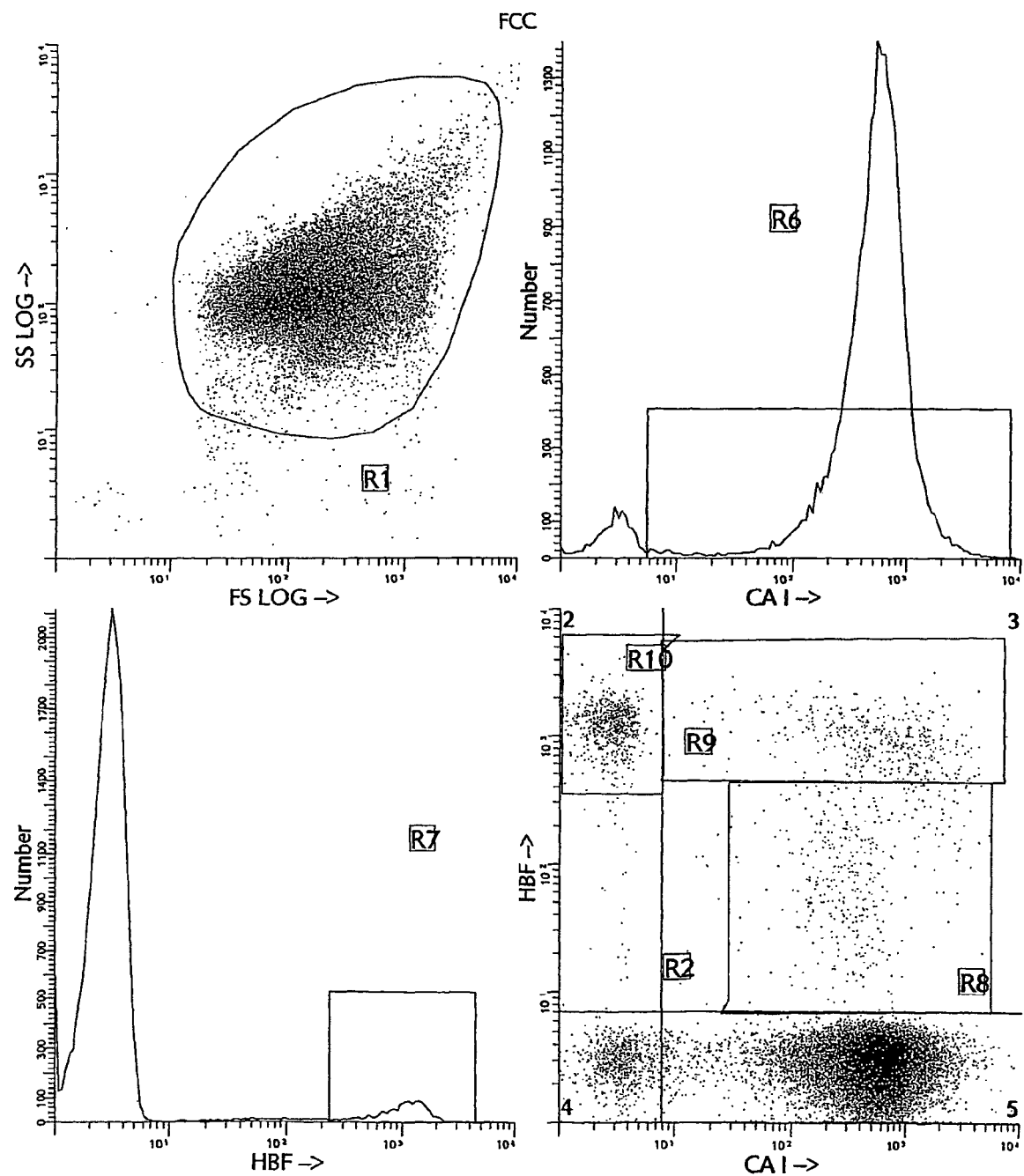
FIG. 3 cytograms are representative of 5% cord blood mixed with normal adult blood and stained with antibodies directed to HbF and erythrocyte-specific CA 1. The distributions of fetal HbF+++ cells, fetal HbF++/CA++ cells, adult HbF+/CA++ or F cells, and adult HbF−−/CA++ cells, are indicated in the different quadrants of the final cytogram.

The imprecise separation of HbF-containing F cells from the true HbF-containing fetal cells is demonstrated in the cytograms of FIG. 2. The fact that it is difficult to set an accurate region on the fetal cells without the interfering F cells, leads to the overestimation of the true population of fetal HbF-containing cells. Especially when the number of fetal cells is low (0.4-0.6%), the true count of fetal cells in a background of contaminating F cells with variable amounts of HbF is not accurate. The flow cytometric results of the combination of the two different red blood cell markers HbF and CA, as presented in FIG. 3, demonstrated that most fetal RBCs with a high HbF content and no CA could be well separated from interfering adult F cells with a lower HbF content but containing high amounts of CA. Adult RBCs with no HbF were, as expected, only positive for CA. Another small but not unexpected population of fetal cells, with a high HbF content and lower CA, was detected next to the fetal cell population and also clearly separated from the F cells. Both the populations of fetal cells combined together resulted in the true count of fetal RBCs in cord blood and mixtures of cord and adult blood.

Figure 4:
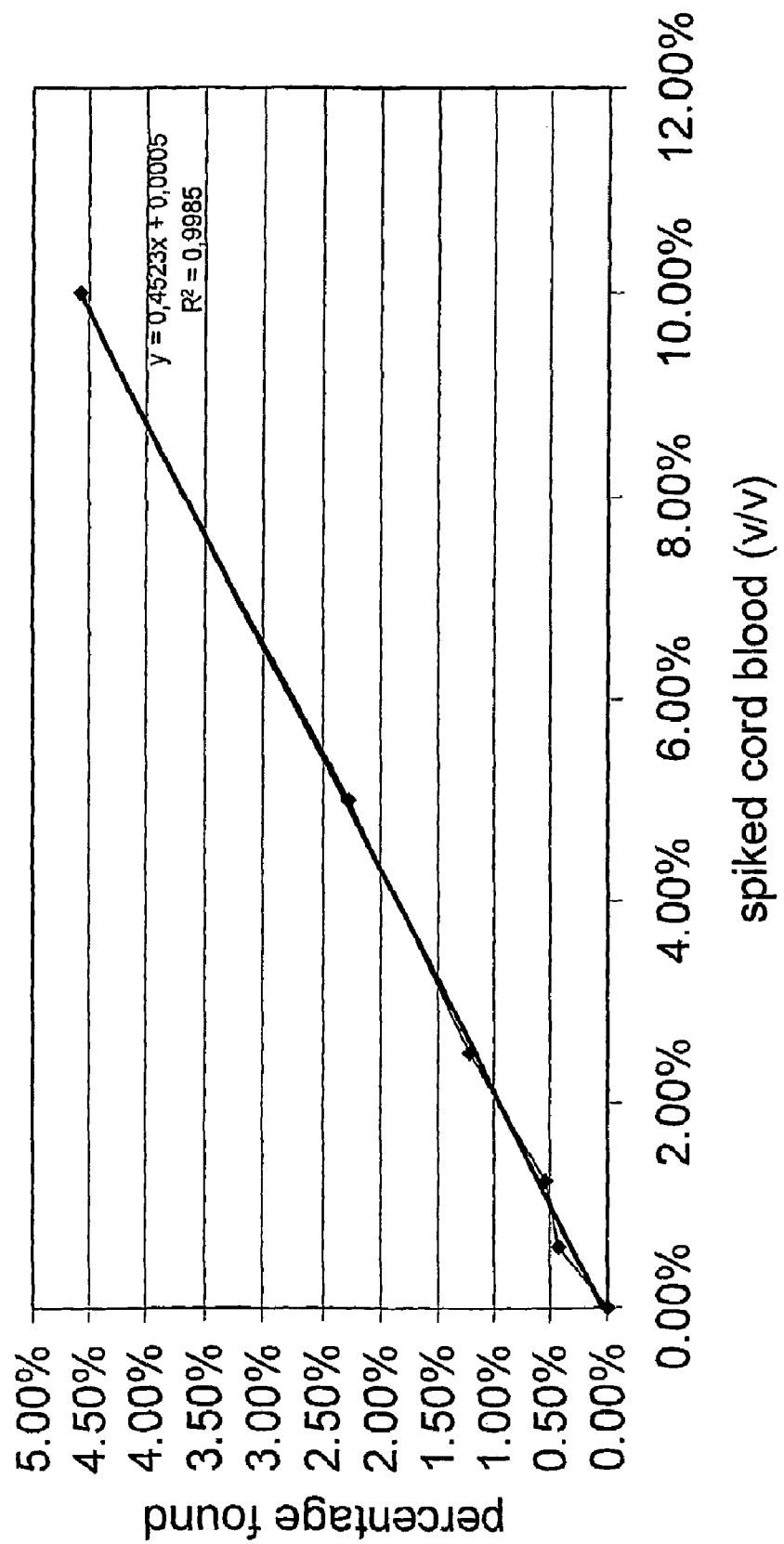
FIG. 4 is a linearity plot of mixed cord blood experiments. The antibodies, anti-HbF and anti-CA are used to detect the percentage of fetal red blood cells in a background of normal adult blood. The plot shows that the detection and linearity is accurate between at least the 0.1% and 10% of spiked cord blood.

The linearity and precision of the dual-color flow cytometric method was studied in mixtures of cord blood and whole blood from non-pregnant adults. As shown in FIG. 4, excellent linearity for the method was observed by serial dilutions of mixtures of cord blood and adult blood (n=10), with a fetal cell frequency range of 0 to 5%. Precision of the method was determined by performing an analysis on the same preparation of mixtures of cord and adult blood within a five-day period. The precision of all the samples consistently resulted in a coefficient of variation (CV) of <5%. Therefore, the new flow cytometric method demonstrated an excellent assay performance and was observed to be linear and precise both above and below the clinically important fetal cell frequency of approximately 0.6%. Linearity of measurement was determined for samples consisting of different ratios of cord blood mixed with normal adult blood in the range of 0.0-10% positive cord blood cells (HbF/CA). Nine months old cord blood consists of 85% fetal RBCs. The linear regression method was used to plot the known expected values versus the observed values for the percent of double-labeled fetal cells determined by the double-fluorescent cytometric method.

Figure 5:
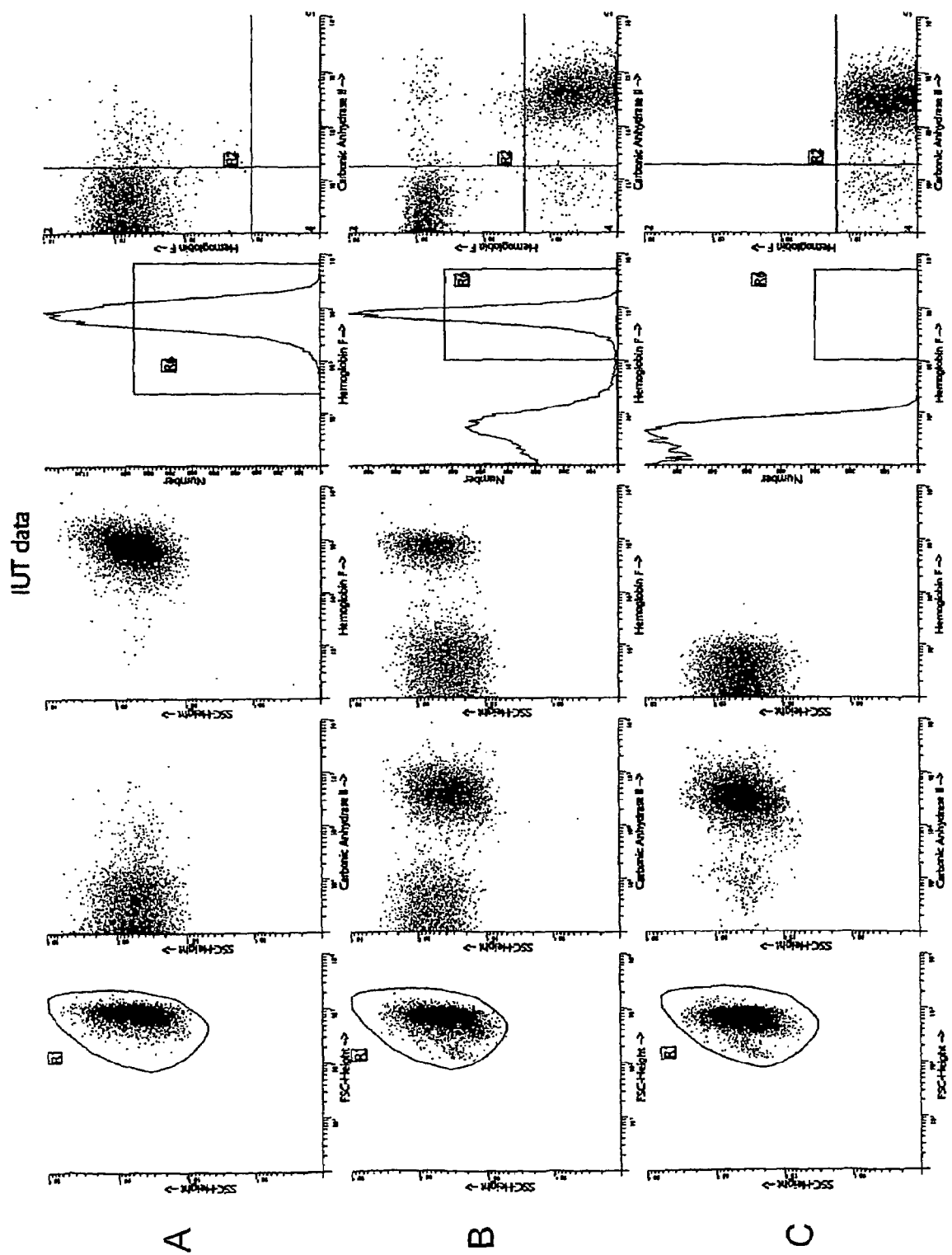
FIG. 5 contains data of an intrauterine transfusion (IUT) as detected with anti-HbF and anti-CA antibodies. Part A cytograms demonstrate the HbF-containing red blood cell population from a blood sample of the fetus. Part B cytograms demonstrate the detection of the fetal and adult red blood cell populations in the blood of the fetus after a 50% transfusion with the adult donor blood. Part C cytograms demonstrate the CA-containing red blood cell population present in the adult donor blood sample.

FIG. 5 shows that the method provided herein for distinguishing between subsets of red blood cells in a sample is also advantageously used to monitor the efficacy of intrauterine blood transfusion. The cytograms demonstrate a clear distinction between red blood cell populations in an adult donor blood sample and in a fetal blood sample before and after a transfusion with the donor blood.

Our studies indicate that the use of a second antibody for the detection of CA, preferably in combination with the HbF marker or with another determinant of essentially fetal cells, provides a more detailed discrimination of the different fetal and adult RBC populations and results in an improvement in the ability to determine fetal RBC frequency.

Bibliography

1. Sebring, E. S., Polesky, H. F. 1990. Fetomaternal hemorrhage: incidence, risk factors, time of occurrence, and clinical effects. Transfusion 30:344-357.
2. Garratty, G., and Arndt, P. A. 1999. Applications of flow cytofluorometry to red blood cell immunology. Cytometry (Communications in Clinical Cytometry) 38:259-267.
3. Nance, S. J., Nelson, J. M., Arndt, P. A., et al. 1989. Quantitation of Feto-maternal hemorrhage by flow cytometry, a simple and accurate method. Am. J. Clin. Pathol. 91:288-292.
4. Lee, D., Contreras, M., Robson, S. C., Rodeck, C. H., Whittle, M. J. 1999. Recommendations for the use of anti-D immunoglobulin for Rh prophylaxis. Transf. Med. 9:93-97.
5. Polesky, H., Sebring, E. 1981. Evaluation of methods for detection and quantitation of fetal cells and their effect on RhIgG usage. Am. J. Clin. Pathol. 76:525-529.
6. Kleihauer, P., Braun, H., and Betke, K. 1957. Demonstration of fetal hemoglobin in erythrocytes of a blood smear. Klin. Wochenschr. 35:637-638.
7. Davis, B. H., Olsen, S., Bigelow, N. C., Chen, J. C. 1998. Detection of fetal red cells in fetomaternal hemorrhage using a fetal hemoglobin monoclonal antibody by flow cytometry. Immunohematology 38:749-756.
8. Johnson, P. R., Tait, R. C., Austin, E. B., et al. 1995. Flow cytometry in diagnosis and management of large fetomaternal haemorrhage. J. Clin. Pathol. 48:1005-1008.
9. Garratty, G., Arndt, P. 1994. Applications of flow cytofluorometry to transfusion science. Transfusion 35:157-178.
10. Nelson, M., Popp, H., Horky, K., Forsyth, C., Gibson, J. 1994. Development of a flow cytometric test for the detection of D-positive fetal cells after foetalmaternal hemorrhage and a survey of the prevalence in D-negative women. Immunohematology 10:55-59.
11. Medearis, A. L. Hensleigh, P. A., Parks, D. R., Herzenberg, L. A. 1984. Detection of fetal erythrocytes in maternal blood post partum with the fluorescence-activated cell sorter. Am. J. Obstet. Gynecol. 148:290-295.
12. Lloyd-Evans, P., Kumpel, B. M., Bromelow, I., Austin, E., Taylor, E. 1996. Use of a directly conjugated monoclonal anti-D (BRAD-3) for quantification of fetomaternal hemorrhage by flow cytometry. Transfusion 36:432-437.
13. Corsetti, J. P., Cox, C., Leary, J. F., Cox, M. T., Blumberg, N., Doherty, R. A. 1987. Comparison of quantitative acid-elution technique and flow cytometry for detecting fetomaternal hemorrhage. Ann. Clin. Lab. Sci. 17:197-206.
14. Navenot, J. M., Merghoub, T., Ducrocq, R., Krishnamoorthy, B., Blanchard, D. 1998. A new method for quantitative determination of fetal hemoglobin-containing red blood cells by flow cytometry: application to sickle cell disease. Cytometry 32:186-190.
15. Nelson, M., Zarkos, K., Popp, H., Gilson, J. 1998. A flow-cytometric equivalent of the Kleihauer test. Vox Sang. 75:234-241.
16. Davis, B. H., Olsen, S., Bigelow, N. C., Chen, J. C. 1998. Detection of fetal red cells in fetomaternal hemorrhage using a fetal hemoglobin monoclonal antibody by flow cytometry. Transfusion 32:749-756.
17. Mundee, Y., Bigelow, N. C., Davis, B. H., Porter, J. B. 2000. Simplified flow cytometric method for fetal hemoglobin containing red blood cells. Cytometry 42:389-393.
18. Bernini, L. F., Kanhai, H. H. H., Losekoot, M., Giordano, P., Harteveld, C. L. 1994. Prenatal diagnosis of homozygous a-thalassemia by an immunological method. Annals New York Academy of Sciences. 731:193-196.
19. Boriack-Sjodin, P. A., Zeitlin, S., Chen, H. H., Crenshaw, L., Gross, S., Dantanarayana, A., Delgado, P., May, J. A., Dean, T., Christianson, D. W. 1999. Structural analysis of inhibitor binding to human carbonic anhydrase II. Protein Sci. 12:2483-2489.
20. Brubaker, D. K., Mao, F., Gay, C. V. 1999. Localization of carbonic anhydrase in living osteoclasts with bodipy 558/568-modified acetazolamide, a thiadiazole carbonic anhydrase inhibitor. J. Histochem. Cytochem. 4:545-550.
21. Yu, H., Ernst, L., Wagner, M., Waggoner, A. 1992. Sensitive detection of RNAs in single cells by flow cytometry. Nucl. Acids Res. 1:83-88.
22. Lewis, D. E., Schober, W., Murrell, S., Nguyen, D., Scott, J., Boinoff, J., Simpson, J. L., Bischoff, F. Z., Elias, S. 1996. Rare event selection of fetal nucleated erythrocytes in maternal blood by flow cytometry. Cytometry 23:218-227.

What is claimed is:

1. A diagnostic kit for the discrimination of subsets of erythrocytes, said diagnostic kit comprising:
a first marker antibody reactive with hemoglobin F of a red blood cell, and
a second antibody reactive with carbonic anhydrase CAII of a red blood cell, and
wherein said first and second antibodies each comprise a label that is different and distinguishably distinct from each other as detected by flow cytometry so as to detect reactivity of the first and second antibodies with cells using flow cytometry.

2. A reagent mixture for use in the discrimination of subsets of erythrocytes, said mixture comprising a first antibody reactive with hemoglobin F of a red blood cell and a second antibody reactive with carbonic anhydrase CAII of a red blood cell and
wherein said first and second antibodies each comprise a label that is different and distinguishably distinct from each other as detected by flow cytometry so as to detect reactivity of the first and second antibodies with cells by flow cytometry.

3. A diagnostic kit for the discrimination of subsets of erythrocytes, the diagnostic kit comprising:
a first antibody reactive with hemoglobin F of a red blood cell, and
a second antibody reactive with a carbonic anhydrase of a red blood cell, and
wherein the first and second antibodies each comprise a label that is different and distinguishably distinct from each other as detected by flow cytometry so as to detect reactivity of the first and second antibodies with cells by flow cytometry.

4. A reagent mixture for use in the discrimination of subsets of erythrocytes, said mixture comprising a first antibody reactive with hemoglobin F of a red blood cell and a second antibody reactive with a carbonic anhydrase of a red blood cell and
wherein the first and second antibodies each comprise a label that is different and distinguishably distinct from each other as detected by flow cytometry so as to detect reactivity of the first and second antibodies with cells by flow cytometry.

* * * * *